(12) United States Patent
Monstadt et al.

(10) Patent No.: US 9,198,665 B2
(45) Date of Patent: Dec. 1, 2015

(54) MICRO-SPIRAL IMPLANTATION DEVICE

(75) Inventors: Hermann Monstadt, Bochum (DE); Achim Flesser, Mettmann (DE); Ralf Hannes, Dortmund (DE)

(73) Assignee: Covidien LP, Mansfield, MA (US)

( * ) Notice: Subject to any disclaimer, the term of this patent is extended or adjusted under 35 U.S.C. 154(b) by 911 days.

(21) Appl. No.: 13/284,816

(22) Filed: Oct. 28, 2011

(65) Prior Publication Data

US 2012/0116442 A1 May 10, 2012

Related U.S. Application Data

(63) Continuation of application No. 11/575,796, filed as application No. PCT/EP2004/010612 on Sep. 22, 2004, now Pat. No. 8,845,676.

(51) Int. Cl.
*A61M 29/00* (2006.01)
*A61B 17/12* (2006.01)

(52) U.S. Cl.
CPC ....... *A61B 17/12022* (2013.01); *A61B 17/1215* (2013.01); *A61B 2017/12063* (2013.01)

(58) Field of Classification Search
CPC ........... A61B 17/1214; A61B 17/1215; A61B 17/12154
USPC .................. 606/108, 151, 157, 191, 200, 194
See application file for complete search history.

(56) References Cited

U.S. PATENT DOCUMENTS

| 3,174,851 A | 3/1965 | Buehler et al. |
|---|---|---|
| 3,334,629 A | 8/1967 | Colm |
| 3,753,700 A | 8/1973 | Harrison et al. |
| 3,834,394 A | 9/1974 | Hunter et al. |
| 4,085,757 A | 4/1978 | Pevsner |
| 4,311,146 A | 1/1982 | Wonder |
| 4,327,734 A | 5/1982 | White, Jr. |
| 4,341,218 A | 7/1982 | U |

(Continued)

FOREIGN PATENT DOCUMENTS

| CN | 1668250 A | 9/2005 |
|---|---|---|
| DE | 4445715 | 6/1996 |

(Continued)

OTHER PUBLICATIONS

Henkes et al., Neurosurgery 54, No. 2, 268 (2004).

(Continued)

*Primary Examiner* — Victor Nguyen
*Assistant Examiner* — Kevin Everage
(74) *Attorney, Agent, or Firm* — Elizabeth A. O'Brien, Esq.

(57) ABSTRACT

The invention relates to a device for the implantation of microcoils into body cavities and blood vessels, in particular aneurysms, with said microcoils comprising wires forming a plurality of windings, at least one microcoil serving as occlusion helix for the occlusion of the body cavity or blood vessel, and the device consisting of a catheter, one or several microcoils movably arranged in longitudinal direction within the catheter and at least one securing means passing at least partially through the lumen of the occlusion helix, with said securing means being fixed in its end areas inside the microcoils. Such a fixation of the securing means is achieved in at least one end area by providing a frictional connection with the microcoil in such a manner that this connection is detachable from the microcoil when a certain tensile force acting on the securing means is exceeded.

6 Claims, 4 Drawing Sheets

(56) References Cited

U.S. PATENT DOCUMENTS

| | | | |
|---|---|---|---|
| 4,346,712 A | 8/1982 | Handa et al. |
| 4,364,392 A | 12/1982 | Strother et al. |
| 4,402,319 A | 9/1983 | Handa et al. |
| 4,441,495 A | 4/1984 | Hicswa |
| 4,494,531 A | 1/1985 | Gianturco |
| 4,517,979 A | 5/1985 | Pecenka |
| 4,545,367 A | 10/1985 | Tucci |
| 4,638,803 A | 1/1987 | Rand |
| 4,677,191 A | 6/1987 | Tanaka et al. |
| 4,735,201 A | 4/1988 | O'Reilly |
| 4,781,177 A | 11/1988 | Lebigot |
| 4,787,899 A | 11/1988 | Lazarus |
| 4,819,637 A | 4/1989 | Dormandy, Jr. et al. |
| 4,832,055 A | 5/1989 | Palestrant |
| 4,944,746 A | 7/1990 | Iwata et al. |
| 4,957,501 A | 9/1990 | Lahille et al. |
| 4,990,155 A | 2/1991 | Wilkoff |
| 4,994,069 A | 2/1991 | Ritchart et al. |
| 5,002,556 A | 3/1991 | Ishida et al. |
| 5,026,377 A | 6/1991 | Burton et al. |
| 5,035,706 A | 7/1991 | Giantureo et al. |
| 5,037,427 A | 8/1991 | Harada et al. |
| 5,062,829 A | 11/1991 | Pryor et al. |
| 5,104,399 A | 4/1992 | Lazarus |
| 5,108,407 A | 4/1992 | Geremia et al. |
| 5,109,867 A | 5/1992 | Twyford, Jr. |
| 5,122,136 A | 6/1992 | Guglielmi et al. |
| 5,133,731 A | 7/1992 | Butler et al. |
| 5,133,732 A | 7/1992 | Wiktor |
| 5,147,370 A | 9/1992 | McNamara et al. |
| 5,167,624 A | 12/1992 | Butler et al. |
| 5,181,921 A | 1/1993 | Makita et al. |
| 5,192,301 A | 3/1993 | Kamiya et al. |
| 5,211,658 A | 5/1993 | Clouse |
| 5,217,484 A | 6/1993 | Marks |
| 5,222,970 A | 6/1993 | Reeves |
| 5,224,953 A | 7/1993 | Morgentaler |
| 5,226,911 A * | 7/1993 | Chee et al. .............. 606/191 |
| 5,234,437 A | 8/1993 | Sepetka |
| 5,250,071 A | 10/1993 | Palermo |
| 5,256,146 A | 10/1993 | Ensminger et al. |
| 5,261,916 A | 11/1993 | Engelson |
| 5,263,964 A | 11/1993 | Purdy |
| 5,282,806 A | 2/1994 | Haber et al. |
| 5,304,194 A | 4/1994 | Chee et al. |
| 5,304,195 A | 4/1994 | Twyford, Jr. et al. |
| 5,312,415 A | 5/1994 | Palermo |
| 5,314,472 A | 5/1994 | Fontaine |
| 5,334,210 A | 8/1994 | Gianturco |
| 5,350,397 A | 9/1994 | Palermo et al. |
| 5,354,295 A | 10/1994 | Guglielmi et al. |
| 5,368,592 A | 11/1994 | Stern et al. |
| 5,382,259 A * | 1/1995 | Phelps et al. .............. 606/151 |
| 5,382,260 A * | 1/1995 | Dormandy et al. ......... 606/151 |
| 5,382,261 A | 1/1995 | Palmaz |
| 5,397,345 A | 3/1995 | Lazarus |
| 5,417,708 A | 5/1995 | Hall et al. |
| 5,423,829 A | 6/1995 | Pham et al. |
| 5,423,849 A | 6/1995 | Engelson et al. |
| 5,443,454 A | 8/1995 | Tanabe et al. |
| 5,443,478 A | 8/1995 | Purdy |
| 5,456,693 A | 10/1995 | Conston et al. |
| 5,476,472 A | 12/1995 | Dormandy, Jr. et al. |
| 5,480,382 A | 1/1996 | Hammerslag et al. |
| 5,485,496 A | 1/1996 | Lee et al. |
| 5,498,227 A | 3/1996 | Mawad |
| 5,499,985 A | 3/1996 | Hein et al. |
| 5,507,769 A | 4/1996 | Marin et al. |
| 5,522,822 A | 6/1996 | Phelps et al. |
| 5,522,836 A | 6/1996 | Palermo |
| 5,527,338 A | 6/1996 | Purdy |
| 5,536,274 A | 7/1996 | Neuss |
| 5,540,680 A | 7/1996 | Guglielmi et al. |
| 5,549,624 A | 8/1996 | Mirigian et al. |
| 5,562,698 A | 10/1996 | Parker |
| 5,569,245 A | 10/1996 | Guglielmi et al. |
| 5,573,520 A | 11/1996 | Schwartz et al. |
| 5,578,074 A | 11/1996 | Mirigian |
| 5,582,619 A | 12/1996 | Ken |
| 5,601,600 A | 2/1997 | Ton |
| 5,624,449 A | 4/1997 | Pham et al. |
| 5,624,461 A | 4/1997 | Mariant |
| 5,626,599 A | 5/1997 | Bourne et al. |
| 5,634,928 A | 6/1997 | Fischell et al. |
| 5,639,277 A | 6/1997 | Mariant et al. |
| 5,643,254 A | 7/1997 | Scheldrup et al. |
| 5,645,558 A | 7/1997 | Horton |
| 5,645,564 A | 7/1997 | Northrup et al. |
| 5,649,949 A | 7/1997 | Wallace et al. |
| 5,658,308 A | 8/1997 | Snyder |
| 5,662,700 A | 9/1997 | Lazarus |
| 5,669,905 A | 9/1997 | Scheldrup et al. |
| 5,669,931 A | 9/1997 | Kupiecki et al. |
| 5,690,666 A | 11/1997 | Berenstein et al. |
| 5,690,667 A | 11/1997 | Gia |
| 5,690,671 A | 11/1997 | McGurk et al. |
| 5,693,067 A | 12/1997 | Purdy |
| 5,695,517 A | 12/1997 | Marin et al. |
| 5,700,258 A | 12/1997 | Mirigian et al. |
| 5,702,361 A | 12/1997 | Evans et al. |
| 5,718,711 A | 2/1998 | Berenstein et al. |
| 5,725,534 A | 3/1998 | Rasmussen |
| 5,725,546 A | 3/1998 | Samson |
| 5,725,552 A | 3/1998 | Kotula et al. |
| 5,733,329 A | 3/1998 | Wallace et al. |
| 5,743,905 A | 4/1998 | Eder et al. |
| 5,746,734 A | 5/1998 | Dormandy, Jr. et al. |
| 5,746,769 A | 5/1998 | Ton et al. |
| 5,749,891 A | 5/1998 | Ken et al. |
| 5,749,894 A | 5/1998 | Engelson |
| 5,749,918 A | 5/1998 | Hogendijk et al. |
| 5,759,161 A | 6/1998 | Ogawa et al. |
| 5,766,219 A | 6/1998 | Horton |
| 5,797,953 A | 8/1998 | Tekulve |
| 5,800,426 A | 9/1998 | Taki et al. |
| 5,800,453 A | 9/1998 | Gia |
| 5,800,455 A | 9/1998 | Palermo et al. |
| 5,814,062 A | 9/1998 | Sepetka et al. |
| 5,830,230 A | 11/1998 | Berryman et al. |
| 5,833,705 A | 11/1998 | Ken et al. |
| 5,843,118 A | 12/1998 | Sepetka et al. |
| 5,846,210 A | 12/1998 | Ogawa et al. |
| 5,851,206 A | 12/1998 | Guglielmi et al. |
| 5,853,418 A | 12/1998 | Ken et al. |
| 5,855,578 A | 1/1999 | Guglielmi et al. |
| 5,891,058 A | 4/1999 | Taki et al. |
| 5,891,128 A | 4/1999 | Gia et al. |
| 5,891,155 A | 4/1999 | Irie |
| 5,891,192 A | 4/1999 | Murayama et al. |
| 5,895,385 A | 4/1999 | Guglielmi et al. |
| 5,895,391 A | 4/1999 | Farnholtz |
| 5,895,410 A | 4/1999 | Forber et al. |
| 5,895,411 A | 4/1999 | Irie |
| 5,911,731 A | 6/1999 | Pham et al. |
| 5,911,737 A | 6/1999 | Lee et al. |
| 5,916,235 A | 6/1999 | Guglielmi |
| 5,919,187 A | 7/1999 | Guglielmi et al. |
| 5,925,037 A | 7/1999 | Guglielmi et al. |
| 5,925,059 A | 7/1999 | Palermo et al. |
| 5,925,060 A | 7/1999 | Forber |
| 5,925,062 A | 7/1999 | Purdy |
| 5,928,226 A | 7/1999 | Guglielmi et al. |
| 5,935,145 A | 8/1999 | Villar et al. |
| 5,935,148 A | 8/1999 | Villar et al. |
| 5,941,249 A | 8/1999 | Maynard |
| 5,941,888 A | 8/1999 | Wallace et al. |
| 5,944,714 A | 8/1999 | Guglielmi et al. |
| 5,944,733 A | 8/1999 | Engelson |
| 5,947,962 A | 9/1999 | Guglielmi et al. |
| 5,947,963 A | 9/1999 | Guglielmi |
| 5,957,948 A | 9/1999 | Mariant |
| 5,964,797 A | 10/1999 | Ho |
| 5,972,019 A | 10/1999 | Engelson et al. |
| 5,976,126 A | 11/1999 | Guglielmi |

(56) References Cited

U.S. PATENT DOCUMENTS

| | | |
|---|---|---|
| 5,976,131 A | 11/1999 | Guglielmi et al. |
| 5,976,152 A | 11/1999 | Regan et al. |
| 5,976,162 A | 11/1999 | Doan et al. |
| 5,980,514 A | 11/1999 | Kupiecki et al. |
| 5,980,550 A | 11/1999 | Eder et al. |
| 5,980,554 A | 11/1999 | Lenker et al. |
| 5,984,929 A | 11/1999 | Bashiri et al. |
| 5,984,944 A | 11/1999 | Forber |
| 5,989,242 A | 11/1999 | Saadat et al. |
| 6,001,092 A | 12/1999 | Mirigian et al. |
| 6,004,338 A * | 12/1999 | Ken et al. ............ 606/191 |
| 6,010,498 A | 1/2000 | Guglielmi |
| 6,013,084 A | 1/2000 | Ken et al. |
| 6,015,424 A | 1/2000 | Rosenbluth et al. |
| 6,017,364 A | 1/2000 | Lazarus |
| 6,017,977 A | 1/2000 | Evans et al. |
| 6,019,757 A | 2/2000 | Scheldrup |
| 6,022,369 A | 2/2000 | Jacobsen et al. |
| 6,024,754 A | 2/2000 | Engelson |
| 6,024,765 A | 2/2000 | Wallace et al. |
| 6,030,413 A | 2/2000 | Lazarus |
| 6,033,423 A | 3/2000 | Ken et al. |
| 6,039,749 A | 3/2000 | Marin et al. |
| 6,056,770 A | 5/2000 | Epstein et al. |
| 6,059,779 A | 5/2000 | Mills |
| 6,059,815 A | 5/2000 | Lee et al. |
| 6,063,070 A | 5/2000 | Eder |
| 6,063,100 A | 5/2000 | Diaz et al. |
| 6,063,104 A | 5/2000 | Villar et al. |
| 6,066,133 A | 5/2000 | Guglielmi et al. |
| 6,066,149 A | 5/2000 | Samson et al. |
| 6,068,644 A | 5/2000 | Lulo et al. |
| 6,074,407 A | 6/2000 | Levine et al. |
| 6,077,260 A | 6/2000 | Wheelock et al. |
| D427,680 S | 7/2000 | Mariant et al. |
| 6,083,220 A | 7/2000 | Guglielmi et al. |
| 6,086,577 A | 7/2000 | Ken et al. |
| 6,090,125 A | 7/2000 | Horton |
| 6,093,199 A | 7/2000 | Brown et al. |
| 6,096,546 A | 8/2000 | Raskin |
| 6,102,917 A | 8/2000 | Maitland et al. |
| 6,102,932 A | 8/2000 | Kurz |
| 6,102,933 A | 8/2000 | Lee et al. |
| 6,113,622 A | 9/2000 | Hieshima |
| 6,117,142 A | 9/2000 | Goodson et al. |
| 6,123,714 A | 9/2000 | Gia et al. |
| 6,126,672 A | 10/2000 | Berryman et al. |
| 6,136,015 A | 10/2000 | Kurz et al. |
| 6,143,007 A | 11/2000 | Mariant et al. |
| 6,146,373 A | 11/2000 | Cragg et al. |
| 6,149,664 A | 11/2000 | Kurz |
| 6,156,061 A | 12/2000 | Wallace et al. |
| 6,159,165 A | 12/2000 | Ferrera et al. |
| 6,159,206 A | 12/2000 | Ogawa |
| 6,165,178 A | 12/2000 | Bashiri et al. |
| 6,165,193 A | 12/2000 | Greene, Jr. et al. |
| 6,165,198 A | 12/2000 | McGurk et al. |
| 6,168,570 B1 | 1/2001 | Ferrera |
| 6,168,592 B1 | 1/2001 | Kupiecki et al. |
| 6,168,610 B1 | 1/2001 | Marin et al. |
| 6,168,615 B1 | 1/2001 | Ken et al. |
| 6,168,622 B1 | 1/2001 | Mazzocchi |
| 6,171,326 B1 | 1/2001 | Ferrera et al. |
| 6,183,491 B1 | 2/2001 | Lulo |
| 6,183,495 B1 | 2/2001 | Lenker et al. |
| 6,187,024 B1 | 2/2001 | Boock et al. |
| 6,187,027 B1 | 2/2001 | Mariant et al. |
| 6,190,373 B1 | 2/2001 | Palermo et al. |
| 6,193,708 B1 | 2/2001 | Ken et al. |
| 6,193,728 B1 | 2/2001 | Ken et al. |
| RE37,117 E | 3/2001 | Palermo |
| 6,202,261 B1 | 3/2001 | Moore et al. |
| 6,203,547 B1 | 3/2001 | Nguyen et al. |
| 6,221,066 B1 | 4/2001 | Ferrera et al. |
| 6,221,086 B1 | 4/2001 | Forber |
| 6,224,610 B1 | 5/2001 | Ferrera |
| 6,231,573 B1 | 5/2001 | Amor et al. |
| 6,231,586 B1 | 5/2001 | Mariant |
| 6,231,590 B1 | 5/2001 | Slaikeu et al. |
| 6,231,597 B1 | 5/2001 | Deem et al. |
| 6,238,403 B1 | 5/2001 | Greene, Jr. et al. |
| 6,238,415 B1 | 5/2001 | Sepetka et al. |
| 6,241,691 B1 | 6/2001 | Ferrera et al. |
| 6,254,592 B1 | 7/2001 | Samson et al. |
| 6,270,495 B1 | 8/2001 | Palermo |
| 6,277,125 B1 | 8/2001 | Barry et al. |
| 6,277,126 B1 | 8/2001 | Barry et al. |
| 6,280,457 B1 | 8/2001 | Wallace et al. |
| 6,281,263 B1 | 8/2001 | Evans et al. |
| 6,287,315 B1 | 9/2001 | Wijeratne et al. |
| 6,287,318 B1 | 9/2001 | Villar et al. |
| 6,293,960 B1 | 9/2001 | Ken |
| 6,296,622 B1 | 10/2001 | Kurz et al. |
| 6,299,619 B1 | 10/2001 | Greene, Jr. et al. |
| 6,299,627 B1 | 10/2001 | Eder et al. |
| 6,306,153 B1 | 10/2001 | Kurz et al. |
| 6,312,405 B1 | 11/2001 | Meyer et al. |
| 6,312,421 B1 | 11/2001 | Boock |
| 6,315,709 B1 | 11/2001 | Garibaldi et al. |
| 6,319,267 B1 | 11/2001 | Kurz |
| 6,322,576 B1 | 11/2001 | Wallace et al. |
| 6,331,184 B1 | 12/2001 | Abrams |
| 6,335,384 B1 | 1/2002 | Evans et al. |
| 6,344,041 B1 | 2/2002 | Kupiecki et al. |
| 6,344,048 B1 | 2/2002 | Chin et al. |
| 6,346,091 B1 | 2/2002 | Jacobsen et al. |
| 6,348,041 B1 | 2/2002 | Klint |
| 6,361,547 B1 | 3/2002 | Hieshima |
| 6,364,823 B1 | 4/2002 | Garibaldi et al. |
| 6,368,338 B1 | 4/2002 | Konya et al. |
| 6,371,972 B1 | 4/2002 | Wallace et al. |
| 6,375,606 B1 | 4/2002 | Garibaldi et al. |
| 6,375,628 B1 | 4/2002 | Zadno-Azizi et al. |
| 6,375,668 B1 | 4/2002 | Gifford et al. |
| 6,375,669 B1 | 4/2002 | Rosenbluth et al. |
| 6,379,329 B1 | 4/2002 | Naglreiter et al. |
| 6,379,374 B1 | 4/2002 | Hieshima et al. |
| 6,383,146 B1 | 5/2002 | Klint |
| 6,383,174 B1 | 5/2002 | Eder |
| 6,383,204 B1 | 5/2002 | Ferrera et al. |
| 6,383,205 B1 | 5/2002 | Samson et al. |
| 6,409,721 B1 | 6/2002 | Wheelock et al. |
| 6,416,535 B1 | 7/2002 | Lazarus |
| 6,416,541 B2 | 7/2002 | Denardo |
| 6,423,085 B1 | 7/2002 | Murayama et al. |
| 6,425,893 B1 | 7/2002 | Guglielmi |
| 6,425,914 B1 | 7/2002 | Wallace et al. |
| 6,428,557 B1 | 8/2002 | Hilaire |
| 6,428,558 B1 | 8/2002 | Jones et al. |
| 6,454,780 B1 | 9/2002 | Wallace |
| 6,458,119 B1 | 10/2002 | Berenstein et al. |
| 6,458,127 B1 | 10/2002 | Truckai et al. |
| 6,458,137 B1 | 10/2002 | Klint |
| 6,464,699 B1 | 10/2002 | Swanson |
| 6,468,266 B1 | 10/2002 | Bashiri et al. |
| 6,475,169 B2 | 11/2002 | Ferrera |
| 6,475,227 B2 | 11/2002 | Burke et al. |
| 6,478,773 B1 | 11/2002 | Gandhi et al. |
| 6,485,524 B2 | 11/2002 | Strecker |
| 6,494,884 B2 | 12/2002 | Gifford, III et al. |
| 6,500,149 B2 | 12/2002 | Gandhi et al. |
| 6,500,190 B2 | 12/2002 | Greene, Jr. et al. |
| 6,511,468 B1 | 1/2003 | Cragg et al. |
| 6,514,264 B1 | 2/2003 | Naglreiter |
| 6,530,934 B1 | 3/2003 | Jacobsen et al. |
| 6,533,801 B2 | 3/2003 | Wallace et al. |
| 6,537,293 B1 | 3/2003 | Berryman et al. |
| 6,540,657 B2 | 4/2003 | Cross, III et al. |
| 6,544,163 B2 | 4/2003 | Wallace et al. |
| 6,544,225 B1 | 4/2003 | Lulo et al. |
| 6,544,268 B1 | 4/2003 | Lazarus |
| 6,544,275 B1 | 4/2003 | Teoh |
| 6,547,804 B2 | 4/2003 | Porter et al. |
| 6,551,305 B2 | 4/2003 | Ferrera et al. |

(56) References Cited

U.S. PATENT DOCUMENTS

| | | |
|---|---|---|
| 6,551,340 B1 | 4/2003 | Konya et al. |
| 6,554,849 B1 | 4/2003 | Jones et al. |
| 6,558,367 B1 | 5/2003 | Cragg et al. |
| 6,569,179 B2 | 5/2003 | Teoh et al. |
| 6,572,628 B2 | 6/2003 | Dominguez et al. |
| 6,575,994 B1 | 6/2003 | Marin et al. |
| 6,585,748 B1 | 7/2003 | Jeffree |
| 6,585,754 B2 | 7/2003 | Wallace et al. |
| 6,589,227 B2 | 7/2003 | Sonderskov Klint |
| 6,589,230 B2 | 7/2003 | Gia et al. |
| 6,589,236 B2 | 7/2003 | Wheelock et al. |
| 6,589,265 B1 | 7/2003 | Palmer et al. |
| 6,592,605 B2 | 7/2003 | Lenker et al. |
| 6,602,261 B2 | 8/2003 | Greene, Jr. et al. |
| 6,602,269 B2 | 8/2003 | Wallace et al. |
| 6,603,994 B2 | 8/2003 | Wallace et al. |
| 6,605,101 B1 | 8/2003 | Schaefer et al. |
| 6,607,538 B1 | 8/2003 | Ferrera et al. |
| 6,607,539 B1 | 8/2003 | Hayashi et al. |
| 6,610,085 B1 | 8/2003 | Lazarus |
| 6,613,074 B1 | 9/2003 | Mitelberg et al. |
| 6,616,617 B1 | 9/2003 | Ferrera et al. |
| 6,620,152 B2 | 9/2003 | Guglielmi |
| 6,623,493 B2 | 9/2003 | Wallace et al. |
| 6,632,241 B1 | 10/2003 | Hancock et al. |
| 6,635,068 B1 | 10/2003 | Dubrul et al. |
| 6,635,069 B1 | 10/2003 | Teoh et al. |
| 6,638,291 B1 | 10/2003 | Ferrera et al. |
| 6,638,293 B1 | 10/2003 | Makower et al. |
| 6,656,173 B1 | 12/2003 | Palermo |
| 6,656,201 B2 | 12/2003 | Ferrera et al. |
| 6,656,218 B1 | 12/2003 | Denardo et al. |
| 6,656,351 B2 | 12/2003 | Boyle |
| 6,660,020 B2 | 12/2003 | Wallace et al. |
| 6,663,607 B2 | 12/2003 | Slaikeu et al. |
| 6,679,903 B2 | 1/2004 | Kurz |
| 6,685,653 B2 | 2/2004 | Ehr et al. |
| 6,689,141 B2 | 2/2004 | Ferrera et al. |
| 6,692,510 B2 | 2/2004 | West |
| 6,702,844 B1 | 3/2004 | Lazarus |
| 6,716,238 B2 | 4/2004 | Elliott |
| 6,723,112 B2 | 4/2004 | Ho et al. |
| 6,743,236 B2 | 6/2004 | Barry et al. |
| 6,743,251 B1 | 6/2004 | Eder |
| 6,766,219 B1 | 7/2004 | Hasey |
| 6,767,358 B2 | 7/2004 | Leonhardt et al. |
| 6,811,561 B2 | 11/2004 | Diaz et al. |
| 6,814,748 B1 | 11/2004 | Baker et al. |
| 6,835,185 B2 | 12/2004 | Ramzipoor et al. |
| 6,849,081 B2 | 2/2005 | Sepetka et al. |
| 6,852,116 B2 | 2/2005 | Leonhardt et al. |
| 6,853,418 B2 | 2/2005 | Suzuki et al. |
| 6,855,153 B2 | 2/2005 | Saadat |
| 6,855,155 B2 | 2/2005 | Denardo et al. |
| 6,860,893 B2 | 3/2005 | Wallace et al. |
| 6,860,901 B1 | 3/2005 | Baker et al. |
| 6,872,218 B2 | 3/2005 | Ferrera et al. |
| 6,878,163 B2 | 4/2005 | Denardo et al. |
| 6,905,503 B2 | 6/2005 | Gifford, III et al. |
| 6,913,618 B2 | 7/2005 | Denardo et al. |
| 6,929,654 B2 | 8/2005 | Teoh et al. |
| 6,945,956 B2 | 9/2005 | Waldhauser et al. |
| 6,958,061 B2 | 10/2005 | Truckai et al. |
| 6,958,068 B2 | 10/2005 | Hieshima |
| 6,964,657 B2 | 11/2005 | Cragg et al. |
| 6,966,892 B2 | 11/2005 | Gandhi et al. |
| 6,994,689 B1 | 2/2006 | Zadno-Azizi et al. |
| 6,994,711 B2 | 2/2006 | Hieshima et al. |
| 7,014,645 B2 | 3/2006 | Greene, Jr. et al. |
| 7,029,486 B2 | 4/2006 | Schaefer et al. |
| 7,029,487 B2 | 4/2006 | Greene, Jr. et al. |
| 7,033,374 B2 | 4/2006 | Schaefer et al. |
| 7,058,456 B2 | 6/2006 | Pierce |
| 7,060,083 B2 | 6/2006 | Gerberding |
| 7,070,607 B2 | 7/2006 | Murayama et al. |
| 7,147,618 B2 | 12/2006 | Kurz |
| 7,169,161 B2 | 1/2007 | Bonnette et al. |
| 7,182,774 B2 | 2/2007 | Barry et al. |
| 7,198,613 B2 | 4/2007 | Gandhi et al. |
| 7,238,194 B2 | 7/2007 | Monstadt et al. |
| 7,300,458 B2 | 11/2007 | Henkes et al. |
| 7,316,701 B2 | 1/2008 | Ferrera et al. |
| 7,323,000 B2 | 1/2008 | Monstdt et al. |
| 7,331,973 B2 | 2/2008 | Gesswein et al. |
| 7,344,558 B2 | 3/2008 | Lorenzo et al. |
| 7,410,482 B2 | 8/2008 | Murphy et al. |
| 7,422,569 B2 | 9/2008 | Wilson et al. |
| 7,473,266 B2 | 1/2009 | Glaser |
| 7,485,122 B2 | 2/2009 | Teoh |
| 7,485,317 B1 | 2/2009 | Murayama et al. |
| 7,524,322 B2 | 4/2009 | Monstdt et al. |
| 7,575,582 B2 | 8/2009 | Gandhi et al. |
| 7,578,826 B2 | 8/2009 | Gandhi et al. |
| RE41,029 E | 12/2009 | Guglielmi et al. |
| 7,691,124 B2 | 4/2010 | Balgobin |
| 7,708,755 B2 | 5/2010 | Davis, III et al. |
| 7,722,636 B2 | 5/2010 | Farnan |
| 7,722,637 B2 | 5/2010 | Barry et al. |
| 7,811,305 B2 | 10/2010 | Balgobin et al. |
| 7,879,064 B2 | 2/2011 | Monstadt et al. |
| 7,896,899 B2 | 3/2011 | Patterson et al. |
| 7,901,444 B2 | 3/2011 | Slazas |
| 7,918,872 B2 | 4/2011 | Mitelberg et al. |
| 8,267,955 B2 | 9/2012 | Patterson et al. |
| 2002/0010481 A1 | 1/2002 | Jayaraman |
| 2002/0065529 A1 | 5/2002 | Laurent et al. |
| 2002/0072712 A1 | 6/2002 | Nool et al. |
| 2002/0072791 A1 | 6/2002 | Eder et al. |
| 2002/0082620 A1 | 6/2002 | Lee |
| 2002/0087184 A1 | 7/2002 | Eder et al. |
| 2002/0120297 A1 | 8/2002 | Shadduck |
| 2002/0128671 A1 | 9/2002 | Wallace et al. |
| 2002/0138095 A1 | 9/2002 | Mazzocchi et al. |
| 2002/0143349 A1 | 10/2002 | Gifford et al. |
| 2002/0169473 A1 | 11/2002 | Sepetka et al. |
| 2003/0014073 A1 | 1/2003 | Bashiri et al. |
| 2003/0040733 A1 | 2/2003 | Cragg et al. |
| 2003/0045901 A1 | 3/2003 | Opolski |
| 2003/0083676 A1 | 5/2003 | Wallace |
| 2003/0130689 A1 | 7/2003 | Wallace et al. |
| 2003/0169473 A1 | 9/2003 | Cotter et al. |
| 2003/0171770 A1 | 9/2003 | Kusleika et al. |
| 2003/0176857 A1 | 9/2003 | Lee |
| 2003/0181927 A1 | 9/2003 | Wallace |
| 2003/0225365 A1 | 12/2003 | Greff et al. |
| 2004/0002731 A1 | 1/2004 | Aganon et al. |
| 2004/0002732 A1 | 1/2004 | Teoh et al. |
| 2004/0002733 A1* | 1/2004 | Teoh ............................ 606/200 |
| 2004/0024394 A1 | 2/2004 | Wallace et al. |
| 2004/0034363 A1 | 2/2004 | Wilson et al. |
| 2004/0034378 A1 | 2/2004 | Monstadt et al. |
| 2004/0078050 A1 | 4/2004 | Monstadt et al. |
| 2004/0098029 A1 | 5/2004 | Teoh et al. |
| 2004/0106946 A1 | 6/2004 | Ferrera et al. |
| 2004/0170685 A1 | 9/2004 | Carpenter et al. |
| 2004/0181256 A1 | 9/2004 | Glaser |
| 2004/0193178 A1 | 9/2004 | Nikolchev |
| 2004/0193206 A1 | 9/2004 | Gerberding et al. |
| 2004/0220563 A1 | 11/2004 | Eder |
| 2004/0220585 A1 | 11/2004 | Nikolchev |
| 2004/0225279 A1 | 11/2004 | Raymond |
| 2005/0021023 A1 | 1/2005 | Guglielmi et al. |
| 2005/0079196 A1 | 4/2005 | Henkes et al. |
| 2005/0222603 A1 | 10/2005 | Andreas et al. |
| 2006/0025801 A1 | 2/2006 | Lulo et al. |
| 2006/0025802 A1 | 2/2006 | Sowers |
| 2006/0036281 A1 | 2/2006 | Patterson et al. |
| 2006/0079926 A1 | 4/2006 | Desai et al. |
| 2006/0116714 A1 | 6/2006 | Sepetka et al. |
| 2006/0135986 A1 | 6/2006 | Wallace et al. |
| 2006/0271097 A1 | 11/2006 | Ramzipoor et al. |
| 2006/0276824 A1 | 12/2006 | Mitelberg et al. |
| 2007/0055302 A1 | 3/2007 | Henry et al. |
| 2007/0173757 A1 | 7/2007 | Levine et al. |

(56) References Cited

U.S. PATENT DOCUMENTS

| | | |
|---|---|---|
| 2007/0185524 A1 | 8/2007 | Diaz et al. |
| 2007/0239193 A1 | 10/2007 | Simon et al. |
| 2008/0045922 A1 | 2/2008 | Cragg et al. |
| 2008/0045997 A1 | 2/2008 | Balgobin et al. |
| 2008/0051803 A1 | 2/2008 | Monjtadt et al. |
| 2008/0097462 A1 | 4/2008 | Mitelberg et al. |
| 2008/0103585 A1 | 5/2008 | Monstadt et al. |
| 2008/0125855 A1 | 5/2008 | Henkes et al. |
| 2008/0220216 A1 | 9/2008 | Unger et al. |
| 2008/0228215 A1 | 9/2008 | Strauss et al. |
| 2008/0228216 A1 | 9/2008 | Strauss et al. |
| 2008/0243106 A1 | 10/2008 | Coe et al. |
| 2008/0300616 A1 | 12/2008 | Que et al. |
| 2008/0306504 A1 | 12/2008 | Win et al. |
| 2008/0319532 A1 | 12/2008 | Monstadt et al. |
| 2009/0177261 A1 | 7/2009 | Teoh et al. |
| 2009/0182268 A1 | 7/2009 | Thielen et al. |
| 2009/0254111 A1 | 10/2009 | Monstadt et al. |
| 2009/0254169 A1 | 10/2009 | Spenser et al. |
| 2009/0270877 A1 | 10/2009 | Johnson et al. |
| 2009/0312748 A1 | 12/2009 | Johnson et al. |
| 2010/0004673 A1 | 1/2010 | Denison et al. |
| 2010/0023105 A1 | 1/2010 | Levy et al. |
| 2010/0030200 A1 | 2/2010 | Strauss et al. |
| 2010/0049165 A1 | 2/2010 | Sutherland et al. |
| 2010/0076479 A1 | 3/2010 | Monstadt |
| 2010/0174269 A1 | 7/2010 | Tompkins et al. |
| 2011/0022003 A1 | 1/2011 | Tekulve |
| 2011/0098814 A1 | 4/2011 | Monstadt et al. |
| 2011/0118777 A1 | 5/2011 | Patterson et al. |
| 2011/0172700 A1 | 7/2011 | Bose et al. |
| 2012/0041470 A1 | 2/2012 | Shrivastava et al. |
| 2012/0065720 A1 | 3/2012 | Strauss et al. |
| 2012/0116442 A1 | 5/2012 | Monstadt et al. |
| 2012/0226305 A1 | 9/2012 | Strauss et al. |
| 2013/0331883 A1 | 12/2013 | Strauss et al. |

FOREIGN PATENT DOCUMENTS

| | | |
|---|---|---|
| DE | 69627243 | 1/1997 |
| DE | 19547617 | 9/1997 |
| DE | 19607451 | 9/1997 |
| DE | 19610333 | 9/1997 |
| DE | 19647280 | 5/2001 |
| DE | 19952387 | 5/2001 |
| DE | 10010840 A1 | 9/2001 |
| DE | 10118017 | 10/2002 |
| DE | 10155191 | 5/2003 |
| EP | 0368571 A2 | 5/1990 |
| EP | 707830 | 4/1996 |
| EP | 711 532 | 5/1996 |
| EP | 717969 A2 | 6/1996 |
| EP | 720 838 | 7/1996 |
| EP | 765636 | 4/1997 |
| EP | 0792623 A1 | 9/1997 |
| EP | 0800791 A1 | 10/1997 |
| EP | 820 726 | 1/1998 |
| EP | 830 873 | 3/1998 |
| EP | 829236 | 3/1998 |
| EP | 853 955 | 7/1998 |
| EP | 865 773 | 9/1998 |
| EP | 882 428 | 9/1998 |
| EP | 904 737 | 3/1999 |
| EP | 914 807 | 5/1999 |
| EP | 941 700 | 9/1999 |
| EP | 941 701 | 9/1999 |
| EP | 992 220 | 4/2000 |
| EP | 1005837 A2 | 6/2000 |
| EP | 1 120 088 | 8/2001 |
| EP | 1 125 553 | 8/2001 |
| EP | 1 129 666 | 9/2001 |
| EP | 1 142 535 | 10/2001 |
| EP | 1 169 969 | 1/2002 |
| EP | 1 188 413 | 3/2002 |
| EP | 1 188 414 | 3/2002 |
| EP | 1 312 312 | 5/2003 |
| EP | 1 316 293 | 6/2003 |
| EP | 1 358 850 | 11/2003 |
| EP | 1 669 032 | 6/2006 |
| EP | 1738698 A2 | 1/2007 |
| EP | 832 607 | 4/2008 |
| JP | 6-246004 | 9/1994 |
| JP | 7-155331 | 6/1995 |
| JP | 7-265431 | 10/1995 |
| JP | 7-284534 | 10/1995 |
| JP | 9-168541 A | 6/1997 |
| JP | 10-201766 | 8/1998 |
| JP | 11-47138 | 2/1999 |
| JP | 11-76249 | 3/1999 |
| JP | 2001-513389 A | 9/2001 |
| JP | 2002-523172 A | 7/2002 |
| JP | 2004-500929 A | 1/2004 |
| JP | 2006-051349 A | 2/2006 |
| JP | 2008-525113 A | 7/2008 |
| WO | WO-88/03817 | 6/1988 |
| WO | WO-89/06984 | 8/1989 |
| WO | WO-90/12616 | 11/1990 |
| WO | WO-91/13592 | 9/1991 |
| WO | WO-92/14408 | 9/1992 |
| WO | WO-92/21400 | 12/1992 |
| WO | WO-93/11719 | 6/1993 |
| WO | WO-93/16650 | 9/1993 |
| WO | WO-94/06502 A2 | 3/1994 |
| WO | WO-94/06503 | 3/1994 |
| WO | WO-94/10936 | 5/1994 |
| WO | WO-94/11051 | 5/1994 |
| WO | WO-94/26175 | 11/1994 |
| WO | WO-95/12367 | 5/1995 |
| WO | WO-96/18343 | 6/1996 |
| WO | WO-96/32153 | 10/1996 |
| WO | WO-96/39950 | 12/1996 |
| WO | WO-97/27888 | 8/1997 |
| WO | WO-98/09570 | 3/1998 |
| WO | WO-98/17183 | 4/1998 |
| WO | WO-98/33452 | 8/1998 |
| WO | WO-98/34546 | 8/1998 |
| WO | WO-98/39048 A2 | 9/1998 |
| WO | WO-98/58590 | 12/1998 |
| WO | WO-99/05977 | 2/1999 |
| WO | WO-99/07292 | 2/1999 |
| WO | WO-99/09893 | 3/1999 |
| WO | WO-99/32037 | 7/1999 |
| WO | WO-99/40852 A1 | 8/1999 |
| WO | WO-99/42038 | 8/1999 |
| WO | WO-99/44538 | 9/1999 |
| WO | WO-99/49812 | 10/1999 |
| WO | WO 99/51151 | 10/1999 |
| WO | WO-99/56636 | 11/1999 |
| WO | WO-00/12016 | 3/2000 |
| WO | WO-00/13593 | 3/2000 |
| WO | WO-00/25680 | 5/2000 |
| WO | WO-00/44306 | 8/2000 |
| WO | WO-00/72781 A2 | 12/2000 |
| WO | WO-01/32085 | 5/2001 |
| WO | WO-01/56500 A2 | 8/2001 |
| WO | WO-01/58382 A2 | 8/2001 |
| WO | WO-01/93937 A2 | 12/2001 |
| WO | WO-02/02018 | 1/2002 |
| WO | WO-02/13705 | 2/2002 |
| WO | WO-02/13706 A2 | 2/2002 |
| WO | WO-02/32496 | 4/2002 |
| WO | WO-02/39911 A2 | 5/2002 |
| WO | WO-02/41753 A2 | 5/2002 |
| WO | WO-02/45596 A2 | 6/2002 |
| WO | WO-02/054943 A2 | 7/2002 |
| WO | WO-02/054980 A2 | 7/2002 |
| WO | WO-02/072168 A2 | 9/2002 |
| WO | WO-02/087449 | 11/2002 |
| WO | WO-02/087651 | 11/2002 |
| WO | WO-02/089676 A2 | 11/2002 |
| WO | WO-02/096273 A2 | 12/2002 |
| WO | WO-02/096301 | 12/2002 |
| WO | WO-03/001970 A2 | 1/2003 |

(56) References Cited

FOREIGN PATENT DOCUMENTS

| | | |
|---|---|---|
| WO | WO-03/007823 | 1/2003 |
| WO | WO-03/017852 | 3/2003 |
| WO | WO-03/034927 | 5/2003 |
| WO | WO-03/039624 A2 | 5/2003 |
| WO | WO-03/041615 | 5/2003 |
| WO | WO-03/053257 | 7/2003 |
| WO | WO-03/053281 | 7/2003 |
| WO | WO-03/072179 | 9/2003 |
| WO | WO-03/073914 A2 | 9/2003 |
| WO | WO-03/077776 | 9/2003 |
| WO | WO-03/077984 | 9/2003 |
| WO | WO-03/082128 | 10/2003 |
| WO | WO-03/086240 | 10/2003 |
| WO | WO-03/092547 | 11/2003 |
| WO | WO-03/099370 | 12/2003 |
| WO | WO-2004/008974 | 1/2004 |
| WO | WO-2004/069059 | 8/2004 |
| WO | WO-2005/113035 A2 | 12/2005 |
| WO | WO-2006/032291 | 3/2006 |
| WO | WO-2006/069123 | 6/2006 |
| WO | WO-2007/121405 | 10/2007 |
| WO | WO-2008/112435 | 9/2008 |
| WO | WO-2008/112436 | 9/2008 |
| WO | WO-2010/117883 | 10/2010 |
| WO | WO-2010/123821 | 10/2010 |

OTHER PUBLICATIONS

Middleton, J.C. & Tipton, A.J. Synthetic biodegradable polymers as orthopedic devices, Biomaterials 21, 2335-46 (2000).

* cited by examiner

MICRO-SPIRAL IMPLANTATION DEVICE

RELATED APPLICATIONS

This application is a continuation of U.S. application Ser. No. 11/575,796, filed Mar. 22, 2007, which is a §371 application of PCT Application No. PCT/EP04/10612, filed Sep. 22, 2004.

The invention relates to a device for the implantation of microcoils into body cavities and blood vessels, in particular aneurysms, with the microcoils comprising wires forming a plurality of windings, at least one microcoil serving as occlusion helix for the occlusion of the body cavity or blood vessel, and the device consisting of a catheter, one or several microcoils movably arranged in longitudinal direction within the catheter and at least one securing means passing at least partially through the lumen of the occlusion helix, with the securing means being fixed in its end areas inside the microcoils. Furthermore, the invention relates to an occlusion helix to be used in connection with the aforedescribed device.

The use of endovascular techniques for the occlusion of body cavities or vessels such as arteries, veins, fallopian tubes or vascular deformities (for example, vascular aneurysms) is known in the art. In this case, the occlusion helix is usually introduced by means of an endovascular insertion wire through a catheter into the cavity to be occluded and deposited therein.

Before placement may commence the occlusion helixes are maneuvered with the help of the catheter through the blood vessel system and, at the target site, advanced out of the catheter and into the cavity to be occluded. Ideally, the separation/severance of the helix follows these steps. In the event of a wrong placement of the occlusion helix or if too large an occlusion helix has been selected for the area to be occluded the helix must then be repositioned or completely retracted into the catheter to subsequently enable such an occlusion helix to be correctly positioned or a correctly sized helix to be placed in position. Maneuvers of this kind involve risks in that parts of the helix are pulled apart and elongated due to the tensile or torsional stresses applied, and in this way become plastically deformed irreversibly, are torn off or broken which may give rise to life-threatening embolism.

To minimize this danger it has been known, inter alia from the European Patent Specification EP 0 792 623 B1, to provide for a polymeric, non-extensible element passing through the lumen of the occlusion helix, the element being permanently attached to the occlusion helix at two places at least. Such a design enables an occlusion helix to be repositioned or retracted into the catheter in such a manner that it is not pulled apart and elongated so that an irreversible deformation can be avoided.

However, this prior-art technique has the disadvantage in that the polymer thread may suddenly break in the event that too high a retraction force is exerted. In such a case the entire tensile load suddenly acts on the occlusion helix itself which may cause not only deformation but may even lead to occlusion helix breakage. Since such a break of the polymer thread may occur all of a sudden the detrimental effects caused in the blood vessel may be considerable and can hardly be controlled.

In view of the problems described above it is therefore the object of the invention to provide a device for the implantation of occlusion helixes that permit a higher degree of safety to be achieved for patients when occlusion helixes are inserted and placed than can be brought about by prior-art means.

According to the invention this objective is reached by providing a device of the kind first mentioned above wherein, in order to achieve a frictional connection, the securing means is fixed in the a microcoil at least in one end area in such a manner that this connection is detachable from the microcoil when a certain tensile force acting on the securing means is exceeded.

By providing only a frictional but not a permanent connection in one end area of the securing means it is ensured that the securing means in this end area is retained in the microcoil by means of frictional forces only. As is doubtlessly possible without difficulty for persons skilled in the art the frictional connection can be designed to involve frictional forces lower than the pull force that must act on the securing means in order to bring about a failure or breakage. On the other hand, the frictional force must be set high enough to enable a retraction and repositioning of the occlusion helix to be performed under normal conditions without problems. In the event the tensile force increases to such an extent that the securing means must be expected to break, the securing means is released at its point of attachment within the microcoil and pulls out of the same so that the frictional connection becomes detached and a failure/breakage of the securing means is avoided. Moreover, the frictional connection will not become detached abruptly as in the case of a failure of the securing means but gradually so that no sudden forces are exerted and permitted to cause negative effects as may be encountered as described with design configurations provided for by prior-art methods. The implantation device provided for by the present invention will cause an "overload slipping clutch" effect.

The frictional connection between the securing means and a microcoil may be established by various methods. One possible design method provides for the securing means to extend between individual or several windings of a microcoil in such a manner that it becomes clamped between the windings. In this case the securing means extends through several gaps between the windings of a microcoil. The strength of the frictional connection can be adjusted via the number of the clamping instances in the gaps between windings provided for the securing means. The securing means in this case may be clamped between the windings on opposites sides of the microcoil resulting in the securing means to cross the microcoil lumen several times in this end area, but may as well extend through the windings of the microcoil on one side only. Another conceivable method of bringing about the frictional connection also provides for the securing means to be wrapped in its end area once or several times around the wire forming the windings of the microcoil so as to produce loops so to speak around the wire forming the microcoil.

Basically, the microcoil to which the securing means is attached may be the occlusion helix itself or microcoils connected to the occlusion helix. In the latter case, the securing means is only indirectly attached to the occlusion helix which offers advantages in that this embodiment is particularly cost effective because customary occlusion helixes may be used for its manufacture. Microcoils attached to the securing means may be inserted into the occlusion helix with the help of customary methods. To connect the microcoil to the occlusion helix methods sufficiently known to persons skilled in the art are suited such as welding, soldering, bonding or mechanical joining processes. Typically, a smaller microcoil is inserted into the occlusion helix both on the distal and on the proximal end with the securing means being attached via the microcoils so inserted.

In accordance with such a conceivable embodiment of the invention at least one additional microcoil is placed in a microcoil serving as occlusion helix, with the outside diameter of the former microcoil corresponding to the inside diameter of the occlusion helix, and the securing means being clamped in at least one end area between the windings of the inner microcoil and the windings of the occlusion helix to enable a frictional connection to be established in this way. An inner microcoil placed in the proximal area may at the same time serve as severance element for the electrolytic detachment of the occlusion helix. The method of electrolytic severance of occlusion helixes is sufficiently known to competent persons skilled in the art and offers many advantages in terms of practicability, safety and cost-effectiveness over other techniques known from prior-art and aimed at separating occlusion helixes. For this purpose, one or several separately spaced electrolytically corrodible locations are provided in the device, expediently within the occlusion helix, with the locations in conjunction with an electrically insulating catheter and a voltage source as well as a cathode usually is positioned on the body surface permitting detachment or severance by electrolytic corrosion. The occlusion helix in this case serves as anode. Aside from this, also prior-art devices are known which provide for the detachment point being arranged in the guide wire.

It is particularly expedient if the occlusion helix, as is known from DE 100 10 840 A1, has several electrolytically corrodible locations, with a securing means being arranged in each segment of the occlusion helix situated between these locations, the securing means preferably extending from one end to the other end of each segment. This embodiment enables the placement of variably sizable lengths of occlusion helixes and at the same time ensures that each individual segment arranged between the electrolytically corrodible points is secured so that a maximum degree of safety is achieved with respect to pre-venting the occlusion helix from being torn off.

Aside from the possibility to clamp the securing means between the windings of the occlusion means and the windings of a microcoil arranged inside the occlusion helix there is also an alternative wherein a thickening element is provided in the end area of the occlusion helix, the outside diameter of which corresponds to the inside diameter of the occlusion helix, and the securing means is clamped between the windings of the occlusion helix and the thickening element. A variety of shapes are conceivable for such a thickening element to be used for the fixation of the securing element with the help of a frictional connection by way of a kind of plug inserted into the occlusion helix.

To bring about the, overload slipping clutch" effect as provided for by the invention it will be sufficient to attach the securing means in one of its end areas to a microcoil by means of a frictional connection whereas the securing means in its other end area is permanently connected to a microcoil. Since from a manufacturing point of view a permanent connection between securing means and microcoil can be produced more easily such a solution is preferred wherein the securing means may be permanently attached both at the proximal and at the distal end of a microcoil. The attachment at the distal end in this case will be less problematic due to manufacturing reasons. It is, of course, also possible to attach the securing means in a microcoil in both end areas by means of a frictional connection so that the securing means can be detached from the microcoil both proximally as well as distally if the pull force acting on the device exceeds a certain limit.

To establish a permanent connection between securing means and microcoil customary methods known from prior-art techniques can be applied such as, for example, gluing, fusing or soldering, depending on the material employed for the securing means. Another way of fixing the securing means at the distal end is to attach it to a thickening element located at the distal end, the thickening element being arranged distally in the microcoil and designed to prevent the securing means from sliding through the microcoil by providing for the diameter of the thickening element to be greater than the inner diameter of the microcoil. The thickening element may, for example, have the form of a sphere or ball. In this manner, a detachment of the securing means from the distal end is prevented without having established a direct, permanent connection between microcoil and securing means.

Moreover, optional combinations of conceivable frictional and permanent connections at the proximal and distal end are possible in the framework of the invention.

As per a particularly preferred embodiment the securing means is a polymer thread or a polymer thread bundle. Such a polymer thread has adequate flexibility so that it can be passed through the gaps between the windings of a microcoil or around the windings of a microcoil. What is more, there are almost no limits to design such a polymer thread to be as thin as required for a given use which makes it possible for the securing means to be used with any conceivable occlusion helixes, in particular those used for intracranial applications. Due to the fact that the gaps between windings of a microcoil are in the range of just 0.008 and 0.01 mm it is an absolute must to provide for securing means that are designed to be as thin as possible.

As polymers numerous biocompatible materials may be employed such as, for example, polyesters, i.e. Dacron, polyamides, in particular nylon, polyolefins, polypropylenes, polybutylenes etc. Another possibility in this context is to incorporate individual metal fibers into the polymer thread with a view to increasing the breaking strength in this manner. Although it is preferred to use polymer threads as securing means the scope of the present invention does by no means exclude the use of other securing means, in particular those on metal basis.

For the production of the polymer threads the use of polyamides, particularly nylon, has turned out to offer special advantages. When using polymer threads as securing means an additional effect may achieved if the polymer threads have thrombogeneous properties. The provision of thrombogeneous threads in occlusion means is basically known in the framework of prior-art techniques, for example from the European Patent Specification EP 0 800 791 A1 or the U.S. Pat. No. 5,382,259. Fibers having a thrombogeneous effect promote the development of thrombi in the body cavity to be occluded, particularly in aneurysms, and in this way make sure the aneurysm can be effectively occluded. A further improvement can be achieved by coating the polymer thread or the securing means and/or the occlusion helix with collagen.

To enable the polymer thread to produce the desired effect it is considered expedient if it projects outwardly from the occlusion helix at one or several locations. The ends of the polymer thread may project from the occlusion helix especially if the polymer threads are clamped in the end area between the windings of the occlusion helix. If the polymer thread extends several times to and fro between the windings several locations will be created in this way where the polymer thread projects from the microcoil which results in the thrombogeneous effect to increase.

Aside from the provision of locations in the end area of the occlusion helix where the polymer thread projects outwardly from it, it is also possible for the polymer thread to project outwardly from the occlusion helix by producing loops at one or several locations between the proximal and distal end of the occlusion helix. Such a loop may extend through the gap between two windings or may also wrap around one or several windings. It is basically possible for the polymer thread to partly project outwardly along the entire length of the occlusion helix and the polymer thread so that it can effectively produce its thrombogeneous effect in this manner. To rule out that such a loop is drawn back into the lumen of the microcoil as soon as a tensile force is exerted on it, it is considered expedient to additionally wrap the polymer thread, adjacent to the loops, around individual windings of the occlusion helix and in this way further secure the position of the loop. Accordingly, the polymer thread may not only fulfill its inventive purpose as securing means but produce a thrombogeneous effect as well.

The positions of the polymer threads are further secured in that the threads, in their end area, extend through the occlusion helix and are appropriately clamped between the windings thereof. The fixation of polymer threads capable of producing a thrombogeneous effect is of special significance because polymer threads that have detached may cause the formation of thrombi in undesirable places and, besides, are difficult to locate. Naturally, the development of thrombi in important blood vessels involves grave health risks for the patients concerned.

Typically, a polymer thread consists of individual fibers which are spun or twisted together. To bring about the thrombogeneous effect it will, therefore, be sufficient if only some of the fibers of a polymer thread project outwardly from the occlusion helix whereas other fibers practically over their entire length extend through the lumen of the occlusion helix to fulfill their inventive purpose as securing means. Individual fibers shorter than the polymer thread itself may also be incorporated into the polymer thread, with the ends of the shorter fibers projecting outwardly from the occlusion helix. In the event individual fibers are available in sufficient number the occlusion means may be provided with outwardly projecting thrombogeneous fibers practically along its entire length. The thrombogeneous fibers in this case as well are secured and fixed in place by passing them through the gaps between the windings of the occlusion helix.

Individual fibers projecting outwardly from the occlusion helix may also be stuck or fused onto the securing means instead of being spun into the polymer thread which serves as securing means. Basically, this may also be done in case the securing means, for example, consists of a metal thread instead of a polymer thread. To enable fibers to be fused it is considered expedient to use for the fibers a thermoplastic material such as polyamides.

Preferably, the securing means of the device according to the invention is a little longer than the particular portion of the microcoil along which it extends. The length of the securing means established in this manner results in a less rigid arrangement in spite of the attachment or fixation inside the microcoil so that in the absence of external forces being exerted the securing means in the microcoil is not subjected to tensile stresses and the flexibility of the microcoil is not restricted. The securing means may as well extend over the entire length of the occlusion helix from the proximal to the distal end without having to make sacrifices in movability and flexibility so that in this way the entire occlusion helix can be secured by preventing it from being torn off. Since the distal tip of an occlusion helix is subjected to particularly high stresses when the helix is placed into a blood vessel the securing means should in fact extend up to the distal tip section of the occlusion helix.

Due to the low traumatizing risks involved platinum and platinum alloys, in particular platinum-iridium alloys, have proven their worth in the manufacture of microcoils and occlusion helixes. The occlusion helix may also be preformed into a superimposed structure which it only assumes in the aneurysm after it has been released from the catheter. In this way the aneurysm is filled up particularly effectively. Preferably, an insertion aid in the form of a guide wire is attached proximally to the occlusion helix.

Aside from a device for the implantation of microcoils into body cavities and blood vessels the invention also relates to the occlusion helix itself which is used in conjunction with the inventive device.

The invention is now described in detail as follows with reference being made to the figures showing the respective embodiments.

Figure 3:
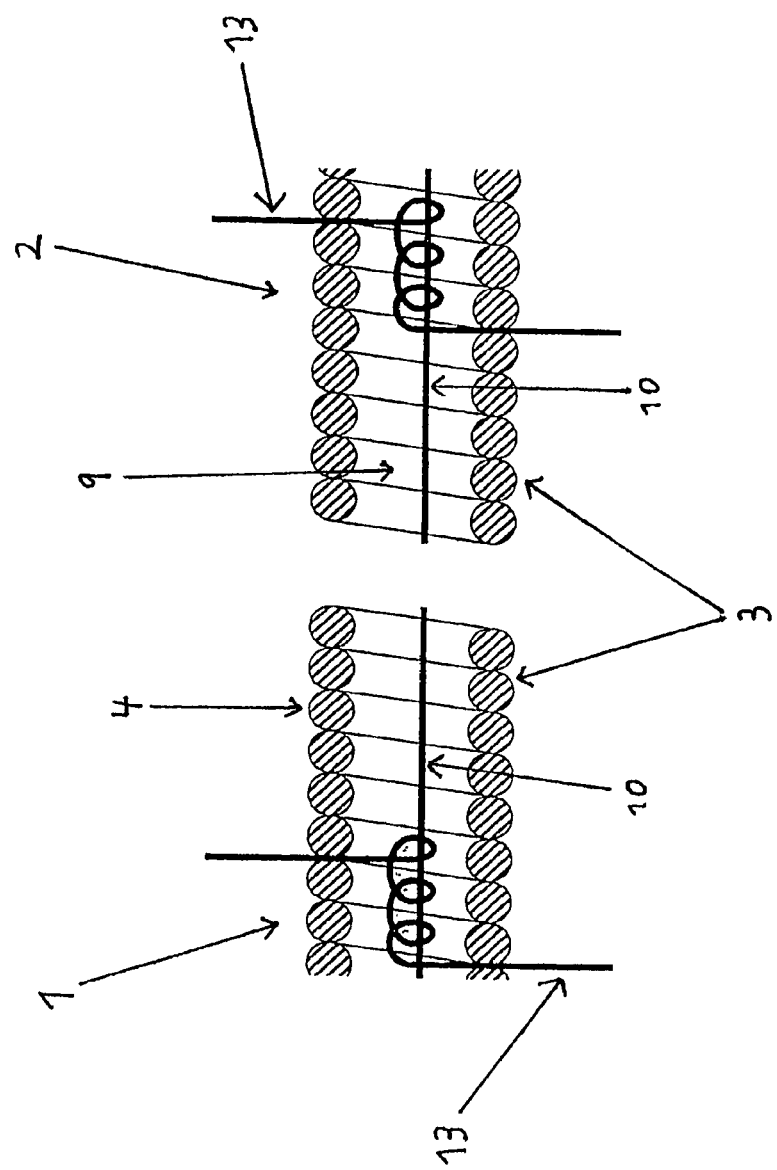
Figure 4:
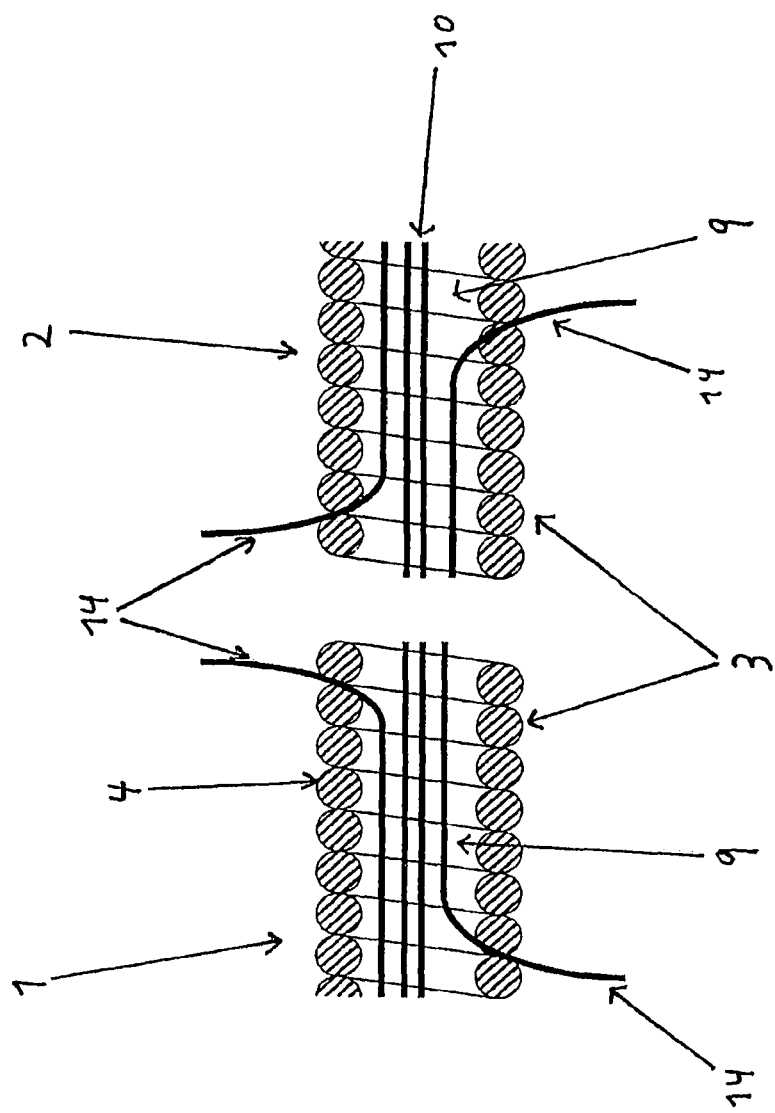

FIG. 3 is a longitudinal section of an inventive device (without catheter, distal tip and severance element) as side view showing the proximal and distal area in accordance with a third embodiment of the invention; and FIG. 4 is a longitudinal section of an inventive device (without catheter, distal tip and severance element) as side view showing the proximal and distal area in accordance with a fourth embodiment of the invention.

Figure 1:
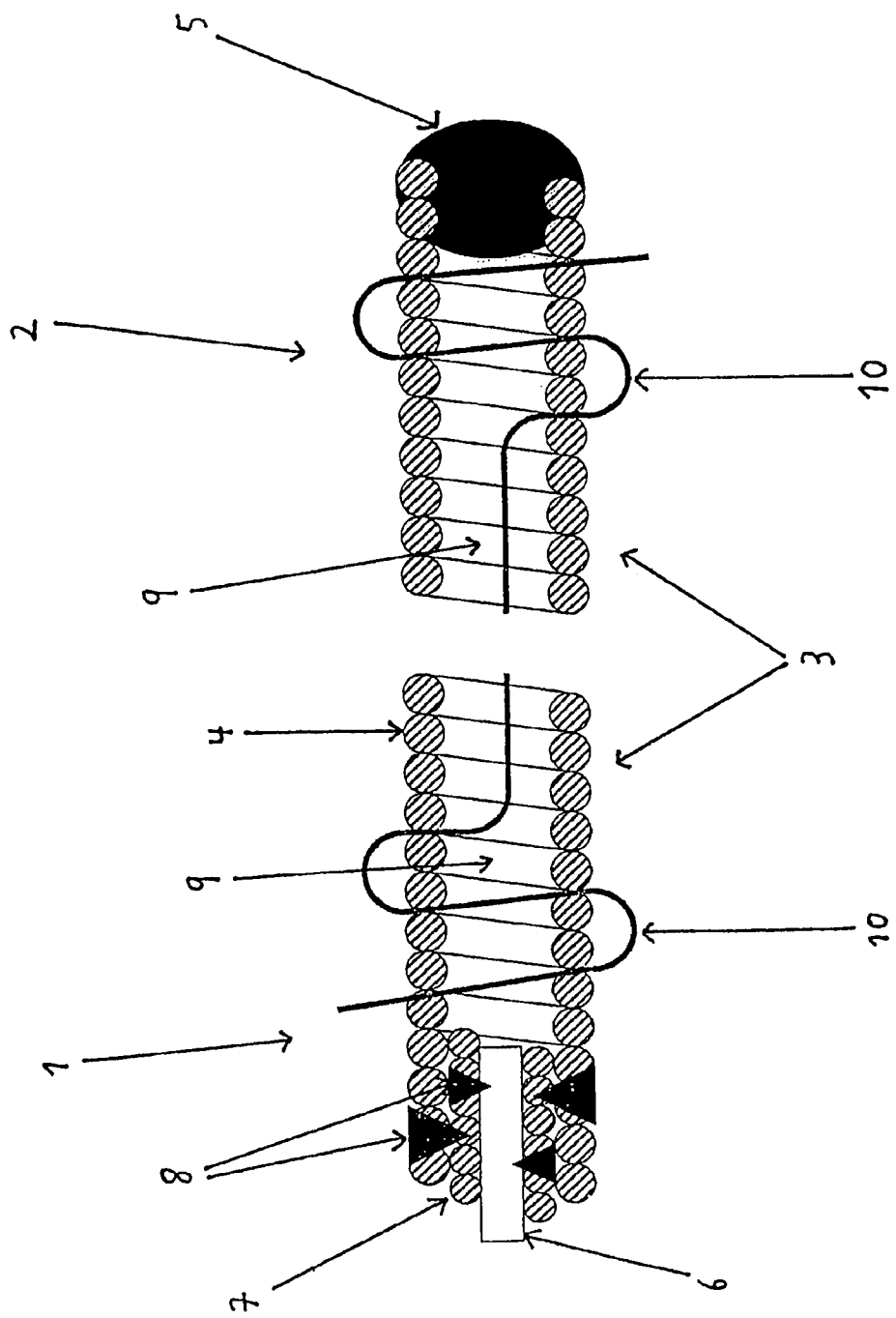
FIG. 1 is a longitudinal section of an inventive device (without catheter) as side view showing the proximal and distal area in accordance with a first embodiment of the invention.

From FIG. 1 the proximal area 1 and the distal area 2 of an occlusion helix 3 can be seen shown as a longitudinal section. The occlusion helix 3 shown here consists of a wire comprising a plurality of windings 4. The distal tip 5 of the occlusion helix 3 is rounded with a view to minimizing aneurysm traumatizing risks. Proximally to the occlusion helix 3 there is a severance element 6 which extends through a microcoil 7 additionally incorporated into the occlusion helix 3. The connection between the additional microcoil 7 and the occlusion helix 3 and between severance element 6 and additional microcoil 7 is made by providing joining points 8, for which purpose various techniques may be employed such as soldering, welding, bonding or mechanical joining methods. The severance element 6 is designed so as to be electrolytically corrodible to enable the occlusion helix 3 by applying a voltage to be released and placed into the aneurysm.

A polymer thread extends through the lumen 9 of the occlusion helix 3 in longitudinal direction and serves as securing means 10, with the thread extending to and fro between the windings 4 of the occlusion helix 3 in several places both in the proximal and in the distal end areas in such a manner that it is secured within the occlusion helix 3 by means of a frictional connection. However, in the event a certain pull force is exceeded the polymer thread 10 may slip out of the windings 4. The force to be overcome to bring about this slipping movement may be adjusted by way of the number of runs of the polymer thread 10 provided between the individual windings 4 of the occlusion helix 3. The maximum tensile or pull force of course increases if the polymer thread 10 extends through the windings 4 more frequently. Moreover, the polymer thread 10 in its end areas projects from the occlusion helix 3 several times which enables it to produce a thrombogeneous effect.

Figure 2:
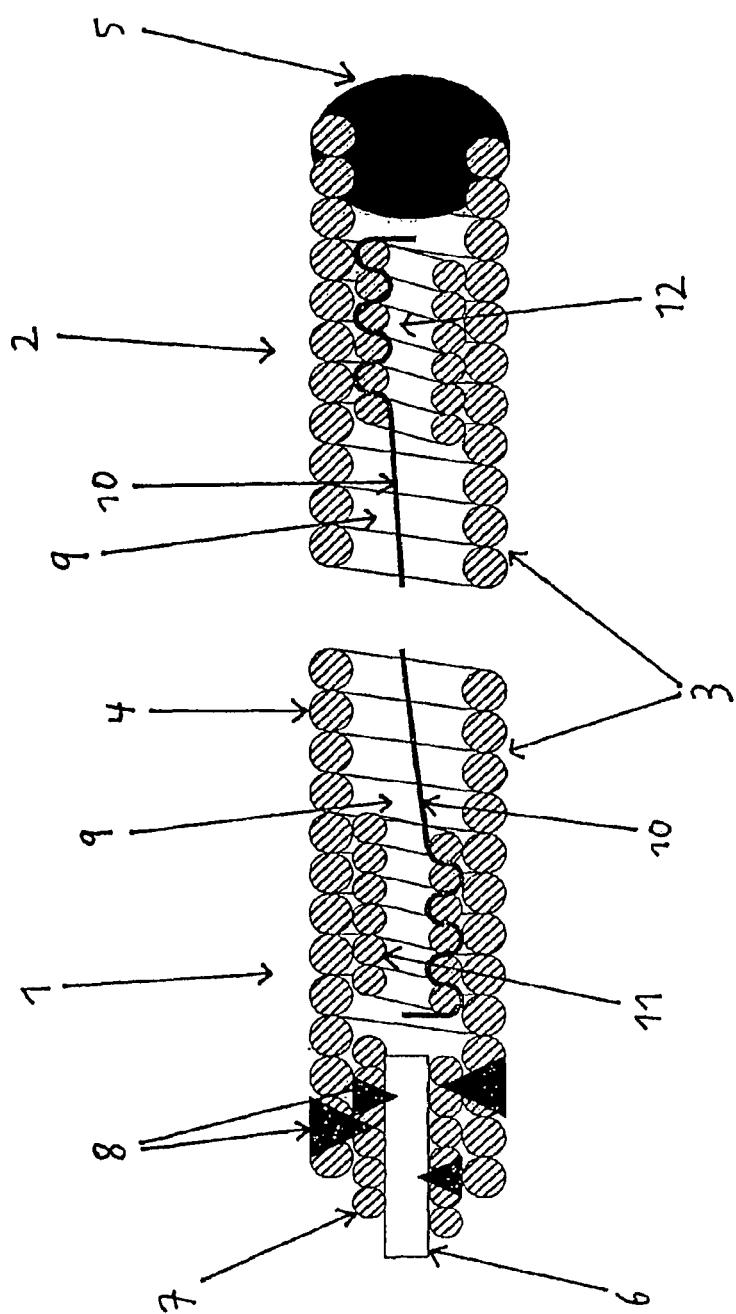
FIG. 2 is a longitudinal section of an inventive device (without catheter) as side view showing the proximal and distal area in accordance with a second embodiment of the invention.

FIG. 2 shows an alternative embodiment of the invention, wherein both in the proximal area 1 and in the distal area 2 of the occlusion helix 3 an additional microcoil 11, 12 has been incorporated, the outer diameter of which corresponding to the inner diameter of the occlusion helix 3. The inner microcoils 11, 12 may be threaded into the occlusion helix 3 and secured by techniques such as laser welding, soldering or bonding to the occlusion helix 3. The polymer thread serving as securing means 10 is clamped both in the distal and in the proximal area between the windings of the inner microcoil 11, 12 and the windings 4 of the occlusion helix 3 and in this manner secured and fixed with the help of a frictional connection. In this case the polymer thread 10 does not project outwardly from the occlusion helix 3 so that an additional thrombogeneous effect cannot be produced. When making use of additional microcoils 11, 12 it is, of course, also possible to provide for an arrangement wherein the polymer thread 10 projects from occlusion helix 3. Furthermore, it is also possible for the inner microcoil 11, 12 to be configured in such a manner that it is connected both with the polymer thread 10 and the severance element 6 by combining the inner microcoils 7 and 11 and 7 and 12.

In accordance with a third embodiment of the invention as illustrated in FIG. 3 the securing means 10 extends through the lumen 9 both in the proximal area 1 and in the distal area 2 of the occlusion helix 3. To enable the inventive effect to be achieved the securing means 10 is secured in the occlusion helix 3 in the proximal and/or distal end area by way of a frictional connection. Moreover, around the securing means 10 individual, shorter polymer threads 13 are wound, the ends of which are permitted to outwardly project from the occlusion helix 3. The projecting polymer threads 13 serve the purpose of bringing about a thrombogeneous effect within the body cavities to be occluded, in particular in aneurysms. In the end areas the polymer threads 13 extend through the windings 4 of the occlusion helix 3 so that they become clamped between the windings 4 and in this way are fixed and secured.

Advantageously, the polymer threads 13 are additionally connected with the securing means 10 in that they are heated up together with the securing means 10 which causes softening of the polymer threads 13 and/or the securing means 10, which may also be a polymer thread, so that a bonding effect finally occurs. There is another possibility of fixing the polymer threads 13 to the securing means 10 in that the securing means 10 is provided with an adhesive coating. For purposes of clarity, the polymer threads 13 in FIG. 3 are shown to merely wrap around the securing means 10 with a permanent fixation not having been illustrated.

As has been shown in FIG. 4, in a further embodiment as well the securing means 10 extends through the lumen 9 of the occlusion means 3 between the proximal area 1 and the distal area 2. For the purpose of producing the inventive effect the securing means 10 is frictionally connected with the occlusion helix 3 in at least one end area. In this case the securing means 10 is a polymer thread which consists of individual fibers. Here, some of the fibers extend virtually over their entire length through the lumen 9 of the occlusion helix 3, whereas other fibers 14 are shorter than the overall length of the securing means 10, with the ends of the other fibers projecting outwardly from the occlusion helix 3. The projecting fibers 14 also serve the purpose of achieving a thrombogeneous effect. The fixation of the thrombogeneous fibers 14 is brought about by passing them through the windings 4 of the occlusion helix 3 such that the fibers 14 in their end area are quasi clamped between the windings 4. It is, furthermore, considered expedient to incorporate the thrombogeneous fibers 14 into the securing means 10 by joining them, using spinning or twisting methods, with the polymer thread forming the securing means 10. Alternatively, the fibers 14 may also be bonded or fused onto the securing means 10.

To illustrate the principle of the invention more clearly, joining the fibers 14 to the securing means 10 by twisting has not been shown in FIG. 4.

What is claimed is:

1. A coil implant, comprising:
   a coil configured for implantation in a vascular structure and having a lumen; and
   a securing member comprising a continuous thread that (a) is coupled to a first end portion of the coil, (b) has a straight portion extending in the lumen along a longitudinal length of the coil, a first undulating portion on a first side of the straight portion, and a second undulating portion on a second side of the straight portion, opposite the first side, (c) is longer than an entire longitudinal length of the coil along which the securing member extends, and (d) is entirely within the lumen.

2. The implant of claim 1, wherein the securing member is coupled to the coil in at least two locations.

3. The implant of claim 2, wherein the securing member extends within the lumen between two of the locations.

4. The implant of claim 3, wherein the securing member has a length between the two locations that is longer than a length of the coil between the two locations.

5. The implant of claim 1, wherein the securing member comprises at least one of a polymer and a metal.

6. The implant of claim 1, wherein, in the absence of external forces applied to the coil, the securing member is not under tensile stress.

* * * * *